United States Patent
Patil

(10) Patent No.: US 12,319,646 B2
(45) Date of Patent: Jun. 3, 2025

(54) LOW BIURET UREA PRODUCTION

(71) Applicant: STAMICARBON B.V., Sittard (NL)

(72) Inventor: Rahul Patil, Sittard (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 18/716,802

(22) PCT Filed: Feb. 21, 2023

(86) PCT No.: PCT/NL2023/050084
§ 371 (c)(1),
(2) Date: Jun. 5, 2024

(87) PCT Pub. No.: WO2023/158314
PCT Pub. Date: Aug. 24, 2023

(65) Prior Publication Data
US 2024/0425449 A1   Dec. 26, 2024

(30) Foreign Application Priority Data
Feb. 21, 2022  (EP) ..................................... 22157781

(51) Int. Cl.
*C07C 273/04* (2006.01)
(52) U.S. Cl.
CPC .................. *C07C 273/04* (2013.01)
(58) Field of Classification Search
None
See application file for complete search history.

(56) References Cited

U.S. PATENT DOCUMENTS

| | | | |
|---|---|---|---|
| 4,314,077 A | 2/1982 | Zardi et al. | |
| 4,701,353 A | 10/1987 | Mutsers et al. | |
| 5,582,656 A | 12/1996 | Kangas et al. | |
| 5,849,952 A | 12/1998 | Carloni et al. | |
| 2015/0086440 A1 | 3/2015 | Scheerder | |
| 2015/0119603 A1 | 4/2015 | Van Den Tillaart et al. | |
| 2018/0195158 A1 | 7/2018 | Gullberg et al. | |
| 2019/0194127 A1 | 6/2019 | Mostert | |
| 2020/0385339 A1 | 2/2020 | Veselovsky et al. | |
| 2020/0306663 A1 | 10/2020 | Poppa | |

FOREIGN PATENT DOCUMENTS

| | | |
|---|---|---|
| WO | 2021137701 A1 | 7/2021 |
| WO | 2003064379 A1 | 8/2021 |

OTHER PUBLICATIONS

International Search Report for International Application No. PCT/NL2023/050084, dated May 9, 2023 (2 pages).
International Preliminary Report on Patentability in International Application No. PCT/NL2023/050084, dated May 23, 2024 (6 pages).
Ullmann's Encyclopaedia of Industrial Chemistry, Chapter Urea, 2010.
Stamicarbon's Ultra Low Energy Design; Technical Paper Sep. 2018.
Jo Meessen, The Stamicarbon low energy urea melt plant, conference paper, Renewable Energy in Fertilizer Industries & Energy Auditing, Amman, Jordan, Apr. 2013.

*Primary Examiner* — Amy C Bonaparte
(74) *Attorney, Agent, or Firm* — Leason Ellis LLP

(57) ABSTRACT

The disclosure pertains to a urea production process wherein carbamate in a medium pressure (MP) urea solution is decomposed in a tube bundle of a high pressure (HP) carbamate condenser and resulting gas is condensed in indirect heat exchange with urea solution to be heated and wherein a high pressure (HP) stripper is preferably operated with relatively low stripping efficiency.

20 Claims, 1 Drawing Sheet

LOW BIURET UREA PRODUCTION

FIELD

The present invention relates to the field of the production of urea from ammonia and carbon dioxide in a urea plant containing a high-pressure synthesis section.

INTRODUCTION

Example urea production plants are illustrated in Ullmann's Encyclopedia of Industrial Chemistry, Chapter Urea, 2010.

US 2015/0119603 describes a method for the production of urea from ammonia and carbon dioxide in a urea plant containing a high-pressure synthesis section with a horizontal pool condenser. The method involves exchanging heat from a high pressure process medium received in a shell section of the pool condenser to a medium pressure urea containing solution received in a first heat exchanging section provided in the pool condenser. The method further comprises exchanging heat from the high pressure process medium to a low pressure steam condensate received in a second heat exchanging section provided in the pool condenser to produce low pressure steam.

US 2020/0306663 describes a urea production process wherein a high pressure carbamate condenser is used for raising steam (e.g. in a tube bundle), which steam is used in embodiments for supplying heat to a step of medium pressure dissociation of urea solution obtained from a stripper or non-stripped urea solution from a reactor.

The production of cooling water from available water sources such as river water in utility plants for urea plants frequently involves steps such as flocculation and conditioning (adding of additives e.g. to prevent fouling and corrosion).

There remains a desire for urea production plants and processes with good energy efficiency and/or with low biuret content of the produced urea.

SUMMARY

The invention pertains in a first aspect to a process for the production of urea from ammonia and carbon dioxide in a urea plant, wherein the urea plant comprises a high pressure (HP) synthesis section comprising a reaction zone, a carbamate condenser and a stripper, wherein the carbamate condenser comprises a shell-and-tube heat exchanger with a shell space and a first and a second horizontal tube bundle, wherein the process comprises: condensing gas from the stripper in the shell space thereby providing a carbamate-containing high pressure liquid stream; expanding a urea solution from said synthesis section to medium pressure (MP) to give a first medium pressure (MP) urea solution comprising carbamate; heating said first MP urea solution in said first tube bundle, thereby decomposing said carbamate comprised in said first MP urea solution; subjecting a fluid stream from the outlet of said first tube bundle to gas/liquid separation to give a second medium pressure (MP) urea solution and a medium pressure (MP) gas stream; condensing said MP gas stream at medium pressure in a first condensation compartment thereby forming carbamate and heating through indirect heat exchanging contact a urea solution to be heated giving a heated urea solution in a first evaporation stage; and raising steam in said second tube bundle, and preferably using said steam to further heat through indirect heat exchanging contact said heated urea solution in a second evaporation stage.

The invention also pertains to a urea production plant comprising: a high pressure (HP) synthesis section comprising a reaction zone, a carbamate condenser and a stripper, wherein the carbamate condenser comprises a shell-and-tube heat exchanger comprising a shell space and a first and a second horizontal tube bundle, wherein the stripper has a gas outlet for gas connected to an inlet of said shell space; an expansion device for expanding urea solution from said synthesis section to medium pressure (MP) to give a first medium pressure (MP) urea solution; wherein the first tube bundle is configured for heating said first MP urea solution thereby decomposing carbamate comprised in said first MP urea solution; a gas/liquid separation unit connected to the outlet of said first tube bundle and having an outlet for a second medium pressure (MP) urea solution and an outlet for a medium pressure (MP) gas stream; a first condensation compartment for condensing said MP gas stream; a first evaporation stage for heating a urea solution to be heated in indirect heat exchanging contact with said first condensation compartment to give a heated urea solution; and a second evaporation stage for further heating the heated urea solution, preferably in indirect heat exchanging contact with steam from the second tube bundle.

The invention also pertains to a method of modifying an existing urea plant, wherein the existing urea plant comprises: a high pressure (HP) synthesis section comprising a reaction zone, a carbamate condenser and a stripper, wherein the carbamate condenser comprises a shell-and-tube heat exchanger comprising a shell space and a first and a second horizontal tube bundle, wherein the stripper has a gas outlet for gas connected to an inlet of said shell space; an expansion device for expanding urea solution from said synthesis section to medium pressure (MP) to give a first medium pressure (MP) urea solution; wherein the first tube bundle is configured for heating said first MP urea solution thereby decomposing carbamate comprised in said first MP urea solution; a gas/liquid separation unit connected to the outlet of said first tube bundle and having an outlet for a second medium pressure (MP) urea solution and an outlet for a medium pressure (MP) gas stream; a first condensation compartment for condensing said MP gas stream; a first evaporation stage for heating a urea solution to be heated in indirect heat exchanging contact with said first condensation compartment to give a heated urea solution; preferably a second evaporation stage for further heating the heated urea solution, in indirect heat exchanging contact with steam from the second tube bundle; wherein the method comprises: adding to the plant a supply line for adding an aqueous stream to the urea solution to be heated upstream of or in the first evaporation stage.

Figure 1:
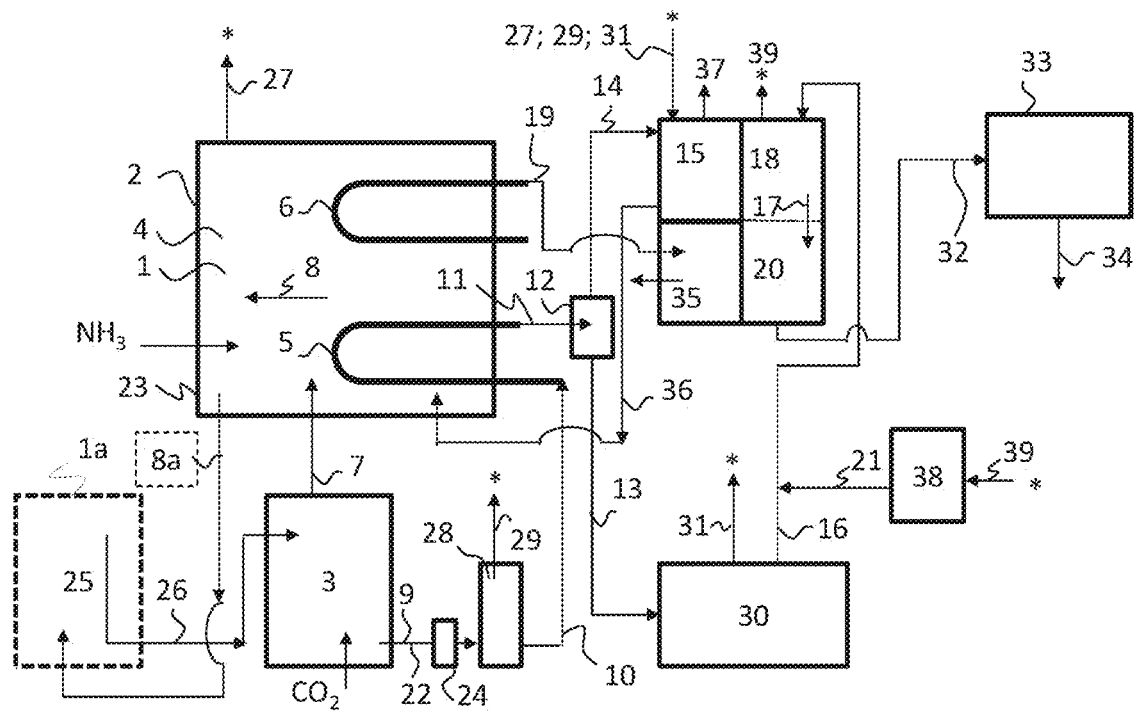
FIG. 1 schematically illustrates an example of a urea production process and a plant according to the invention.

Any embodiments illustrated in the figures are examples only and do not limit the invention.

DETAILED DESCRIPTION

The urea production process is carried out in a urea plant. The urea plant comprises a high pressure (HP) synthesis section. The HP synthesis section comprises a reaction zone, a carbamate condenser and a stripper, all operating at a pressure in a high pressure (HP) range.

The high pressure (HP) stripper is typically provided as a vertical shell-and-tube heat exchanger configured for receiving a urea solution in the tubes at the top and having a gas outlet at the top and an outlet for a stripped urea solution at the bottom, and configured for receiving a heating fluid, such as steam, in the shell. Preferably, the HP stripper is a high pressure (HP) $CO_2$ stripper having an inlet for $CO_2$ used as strip gas in the tubes at the bottom.

In a preferred embodiment with the HP $CO_2$ stripper, the N/C ratio of the urea solution at the reaction zone (or reactor) outlet is e.g. 2.8-3.8, e.g. 2.9-3.2, preferably with a synthesis pressure in the range of 140-150 bar in the synthesis section, wherein the reaction zone (e.g. reactor), the condenser and the stripper preferably form a substantially isobaric loop.

The relatively low N/C ratio at the reaction zone outlet and preferred $CO_2$ HP stripping contribute to the preferred recycle of carbamate from a medium pressure (MP) carbamate condenser to the HP synthesis section without separate $NH_3$ recycle.

In a preferred embodiment, the HP stripper is a shell-and-tube heat exchanger wherein at least some parts of the HP stripper that are in contact with the urea solution in operation (wetted parts) are made of duplex ferritic-austenitic stainless steel, and preferably all wetted parts are made of duplex ferritic-austenitic stainless steel. Suitable duplex stainless steel for wetted parts of the HP stripper includes for example a super duplex steel available as Safurex® steel and having composition 29Cr-6.5Ni-2Mo-N, which steel is also designated by as UNS S32906. In particular, the duplex steel for wetted parts of the HP stripper has for instance the composition (% by mass): C: max. 0.05; Si: max. 0.8; Mn: 0.3-4.0; Cr: 28-35; Ni: 3-10; Mo: 1.0-4.0; N: 0.2-0.6; Cu: max. 1.0; W: max. 2.0; S: max. 0.010; Ce: 0-0.2; balance Fe and normally occurring impurities (composition 1). Preferably, the ferrite content is 30-70% by volume and more preferably 30-55%. More preferably, the steel contains (% by weight): C max. 0.02, Si max. 0.5, Cr 29-33, Mo 1.0 to 2.0, N 0.36 to 0.55, Mn 0.3 to 1.0, balance Fe and (unavoidable) impurities; all in mass %, as described in WO 95/000674 herein incorporated by reference.

More preferably, the duplex stainless steel that is optionally used in particular for the stripper tubes has the composition, in wt. %: C max 0.030; Si max 0.8; Mn max 2.0; Cr 29.0 to 31.0; Ni 5.0 to 9.0; Mo less than 4.0; W less than 4.0; N 0.25 to 0.45; Cu max 2.0; S max 0.02; P max 0.03; balance Fe and unavoidable occurring impurities; and wherein the content of Mo+W is greater than 3.0 but less than 5.0 (composition 2); more preferably wherein the content of Mo+W is greater than 3.0 but less than 4.0; with a preferred steel compositions as described in US 2018/0195158 A1 which is hereby incorporated by reference. A preferred exemplary duplex stainless steel is the steel with designation UNS S83071.

In a particularly preferred embodiment, the stripper tubes are made of the duplex stainless steel with composition 2 specified hereinabove, and at least some, preferably all, of the other wetted parts of the HP stripper are made of duplex stainless steel, preferably of the super duplex steel having composition 1 specified hereinabove.

It has now been found that in preferred embodiments of the process of the present invention, wherein the HP stripper is operated with a preferred stripping efficiency alpha ($\alpha$) of 70% or less, more preferably 65% or less, more preferably 55-65%, and wherein the HP stripper as described above is used wherein at least some parts of the HP stripper that are in contact with the urea solution in operation (wetted parts) are made of duplex ferritic-austenitic stainless steel, and preferably all wetted parts are made of duplex ferritic-austenitic stainless steel, more preferably with stripper tubes of duplex steel having composition 2, very advantageously allows the HP stripper to operate with an expected lifetime of at least 20 years even under oxygen-free conditions. Herein oxygen-free conditions in particular indicate that no passivation oxygen is added, more specifically that no oxygen is added intentionally to any of the $NH_3$ feed and the $CO_2$ feed to the HP synthesis section. Avoiding passivation oxygen provides advantages of improved safety and improved conversion, and for instance advantageously a hydrogen removal reactor for the $CO_2$ feed stream may be omitted.

The HP carbamate condenser is used for condensing the gas stream comprising $NH_3$ and $CO_2$ from the stripper by carbamate condensation. The carbamate condenser is preferably a horizontal pool condenser.

The carbamate condenser is a horizontal carbamate condenser and it is a shell-and-tube heat exchanger. Importantly, the carbamate condenser comprises a first and a second tube bundle. In addition, the carbamate condenser comprises a shell space (shell-side space) between the tubes and the shell. The tube bundles are horizontal and are for instance U-shaped tube bundles with horizontal tube legs. The shell space has an inlet for a gas to be condensed from the stripper thereby forming carbamate. Such a carbamate condenser can be referred to as a pool condenser, in particular as a horizontal pool condenser.

The carbamate condensation reaction in the shell space is exothermic. In operation of the condenser, the tube bundles are submerged in a liquid present in the shell space. The residence time of the liquid in the shell space may permit the urea formation reaction to occur already at least in part in the shell space.

Typically, the horizontal carbamate condenser comprises a sparger arranged in the shell space for distributing gas from the stripper in the shell space. The sparger extends for instance horizontally over the bottom of the shell space for distributing the gas horizontally. Preferably, at least a part of the sparger is arranged below the tube bundles.

In a preferred embodiment, the carbamate condenser with a first and a second horizontal U-shaped tube bundle comprises a reaction zone in the shell space between the shell of the condenser and a bend of the U-shaped tube bundle. In particular, preferably the U-shaped horizontal tube bundles extend over less than 80% or less than 70% of the horizontal length of the shell, or of the shell space, and the remaining part of the shell space provides for said reaction zone in the shell space. Thereby the carbamate condenser and the reaction zone are provided by a single vessel, which can be referred to as a pool reactor. The pool reactor preferably comprises baffles in the shell. Preferably, one of the baffles is configured as an overflow weir providing for gas/liquid separation in the shell space. Preferably, the shell space has a liquid outlet and a separate outlet for gas. In operation, urea formation already takes place in the shell space; in particular the reaction zone may provide for a sufficient residence time of liquid for the urea formation reaction. A urea solution from the shell space of the pool reactor is supplied e.g. directly to the HP stripper. Preferably, a part of the sparger extends horizontally in the reaction zone.

In a preferred embodiment, the horizontal pool condenser comprises a shell-and-tube heat exchanger which comprises a vessel which comprises a shell and at least two tube bundles, wherein the shell encloses a vessel space, wherein the tube bundles comprise tubes having ends. The tube bundles are provided in the vessel space. A shell space is provided between the tubes and the shell. The shell space is confined by the shell. Preferably, the heat exchanger further comprises a redistribution chamber located in said vessel space, more preferably in the shell space. The redistribution chamber comprises a wall for separating a first fluid in the shell space from a second fluid inside the redistribution chamber. Each tube bundle comprises a plurality of tubes. Preferably, the two or more tubes of one of said tube bundles are connected to a single redistribution chamber such that said second fluid can flow between said two or more tubes of the tube bundle and said redistribution chamber. Preferably, the heat exchanger further comprises a duct extending from an opening for the second fluid in said shell through said vessel space to said redistribution chamber. Preferably, the duct extends through the shell space. The duct and the redistribution chamber together provide for fluid communication between the tubes and the opening in the shell. The second fluid can flow between a tube end and said opening for the second fluid in said shell through said redistribution chamber and said duct. Preferably, the wall of the redistribution chamber is separate from the shell. Preferably, the redistribution chamber is spaced apart from the shell. Preferably, the redistribution chambers are box-shaped. Preferably, the redistribution chambers each comprise a first wall provided with bore holes for the tubes and an opposite second wall; preferably, the first and the second wall are both on the outside in fluid communication with the outer surface of the tubes.

Preferably, the condenser comprises, for each of said tubes, two of said ducts including an inlet duct and an outlet duct, and comprises two of said redistribution chambers, including an inlet redistribution chamber for distributing a cooling fluid feed from said inlet duct to a plurality of tubes of said tube bundle and an outlet redistribution chamber for combining a heated cooling fluid from those tubes to said outlet duct. An example of such a carbamate condenser is described in US 2020/0306663. The HP carbamate condenser described therein can be used in the present invention. The construction is particularly advantageous since the first tube bundle in operation comprises corrosive urea solution comprising carbamate in the tubes.

The pool condenser may also comprise a shell-and-tube heat exchanger comprising a tube sheet comprising sleeves extending through the tube sheet. An example is described in US 2015/0086440. The sleeves protect the carbon steel inner part of the tube sheet against a corrosive process medium in the tubes.

In some embodiments, the reaction zone is provided in part or entirely as a vertical urea reactor, typically a vertical urea reactor with an inlet for liquid from the shell space from the HP carbamate condenser at the bottom of the vertical reactor, and typically the vertical urea reactor is provided with means for withdrawing the urea solution from an upper part of the reactor, such as an outlet or downcomer. The reactor is typically provided with trays. In some embodiments, the reaction zone is provided by two units, e.g. in part by a the condenser and in part by the vertical urea reactor. In other embodiments, the reaction zone is provided entirely by a vertical urea reactor. A horizontal urea reactor is also possible.

In some embodiments, the plant does not comprise a vertical urea reactor, and the reaction zone is for instance provided by the same vessel that provides the carbamate condenser, for instance in case of a pool reactor. In some embodiments, a pool reactor is combined with a vertical urea reactor, arranged between the pool reactor and the stripper; the vertical urea reactor then receives liquid from the shell space of the pool reactor. The plant may also comprise two or more reactors in parallel. The vertical urea reactor may comprise one or more inlets for feed $NH_3$ and/or $CO_2$ at the bottom.

The first tube bundle is used for heating the urea solution in the tubes, which urea solution also comprises carbamate. Thereby, at least a part of carbamate is decomposed into $NH_3$ and $CO_2$. The urea solution is present at medium pressure in the tubes and is obtained by expanding a high pressure (HP) urea solution from the synthesis section to medium pressure, optionally with further processing steps such as flashing, to give a first medium pressure (MP) urea solution. Typically, the first tube bundle is configured for heating the first MP urea solution, thereby decomposing carbamate comprised in the first MP urea solution.

The urea solution from the stripper, in particular from the HP $CO_2$ stripper, is e.g. flashed in a flash tank at medium pressure, e.g. 20-30 bar, to give a flash vapour and a flashed urea solution. More preferably, the flash pressure is 23-28 bar, even more preferably 25-28 bar.

The flash vapour is relatively $CO_2$ rich and is supplied, directly or indirectly, to the MP carbamate condenser, to adjust (lower) the N/C ratio in the condenser. Flashing refers to an adiabatic expansion of the urea solution and separation of the released liquid. The flash tank e.g. has an inlet for liquid and an outlet for gas at the top, and an outlet for liquid at the bottom.

The flashed urea solution is optionally further reduced in pressure in the medium pressure range and is supplied to the first tube bundle as the first MP urea solution. Preferably, the flashed urea solution is kept at the same pressure and is supplied to the first tube bundle as the first MP urea solution. The flashing step allows for sending only liquid to the first tube bundle thereby contributing to good distribution of liquid over the tubes.

The urea solution supplied to the first tube bundle optionally originates entirely or in part from the liquid outlet of the HP stripper. Optionally, all urea solution from the reaction zone is supplied to the HP stripper. Optionally, all stripped urea solution is supplied after flashing to the first tube bundle. In an example embodiment, only the stripped urea solution, after optional flashing, is supplied to the first tube bundle. In an example embodiment, all urea solution at the inlet of the first tube bundle originates from the HP stripper. At the outlet of the first tube bundle, a fluid stream is obtained, which is subjected to gas/liquid separation to obtain a second medium pressure (MP) urea solution and a medium pressure (MP) gas stream. The MP urea solution is typically expanded and supplied, directly or indirectly, to a low pressure (LP) recovery section, in particular to a low pressure (LP) decomposer, operating at e.g. 2-8 bar, preferably 4-6 bar.

Preferably, the urea solution from the gas/liquid separation is brought at medium pressure in a counter-current contact with the vapour from the flashing of the stripped urea solution. Preferably, the urea solution is accordingly subjected to an adiabatic medium pressure (MP) stripping with said vapor. This contacting, for example conducted as adiabatic MP stripping, helps to decrease the N/C ratio of the urea solution, which can be advantageous for the carbamate condensation in a low pressure (LP) section, in particular for obtaining a lower N/C ratio in a low pressure (LP) carbamate condenser thereby improving operation of the LP carbamate condenser. The urea solution is expanded to low pressure after the preferred adiabatic MP stripping and then supplied to a low pressure (LP) decomposer. The contacting, for example the adiabatic MP stripping, is in particular useful for preferred embodiments wherein the HP stripper is operated with a preferred relatively low stripping efficiency a. Furthermore, the gas from the MP contacting, preferably the adiabatic MP stripping, is condensed and recycled as a carbamate stream at medium pressure thereby having a relatively lower water content than a low pressure (LP) carbamate stream.

In the LP decomposer, the urea solution is heated to remove more carbamate. The resulting LP urea solution, is optionally subjected to atmospheric flashing and is expanded and preferably supplied at a (sub atmospheric) pressure of typically 0.2-0.5 bara, preferably 0.25-0.35 bara to the first evaporation stage.

A gas from the LP decomposer is typically condensed in the LP carbamate condenser to form a low pressure (LP) carbamate solution. Typically, a stream comprising water is added to the LP carbamate condenser to provide sufficient water to avoid carbamate crystallization in the LP carbamate condenser.

The MP gas stream, obtained from the fluid stream from the first tube bundle, is condensed to form a medium pressure (MP) carbamate solution. This reaction is exothermic and is carried out in a first condensation compartment that is in indirect heat exchanging contact, i.e. through a wall, with a urea solution to be heated to give a heated urea solution. Typically, this urea solution to be heated comes from the LP decomposer; but other sources of the urea solution are also possible, for instance in case of urea plants with two HP synthesis sections in parallel. The condensation is carried out at medium pressure. The MP carbamate solution is recycled to the HP synthesis section.

The MP gas is supplied to the first condensation compartment. An off-gas from the HP carbamate condenser and/or an off-gas from the reaction zone may also be condensed in said first condensation compartment. The gas originating from the flashing of the stripped urea solution may also be supplied, directly or indirectly, to said first condensation compartment. The carbamate solution from an LP recovery section may also be supplied directly or indirectly to said first condensation compartment, to prevent crystallization of carbamate by ensuring a correct water content of the carbamate solution.

The plant comprises for instance an MP carbamate condenser which is a shell-and-tube heat exchanger with urea solution to be heated in tubes and with at least a first and a second condensation compartment in a shell side.

The tubes or parts of the tubes in contact with said first condensation compartment, provide a first evaporation stage for evaporating water from a urea solution. Herein, the term "first evaporation stage" does not exclude the presence of upstream units for water evaporation from the urea solution, for example a pre-evaporator may be present between an LP decomposer and the first evaporation stage.

In preferred embodiments with a supply line for adding an aqueous stream to the urea solution to be heated upstream of or in the first evaporation stage, said supply line is connected in particular to said tubes of said MP carbamate condenser or to a flow line for urea solution to said tubes of said MP carbamate condenser.

The condensation in the first condensation compartment is performed typically at a temperature of 100-125° C., at a shell side outlet, preferably 110° C.-120° C., and/or preferably at 20-30 bar, more preferably at 23-28 bar, even more preferably 25-28 bar.

The N/C ratio of the liquid carbamate stream from the first condensation compartment is preferably in the range 2.1-2.5, preferably 2.2-2.4. Thereby elegantly condensation can be performed at conditions close to the azeotrope ($NH_3$/$CO_2$) conditions, thereby advantageously providing for relatively low water content (as wt. %) necessary in the carbamate solution to prevent crystallization of carbamate at the condensation pressure and temperature.

The temperature may vary over the first condensation compartment, from inlet to outlet (e.g. from bottom to top), e.g. from 140° C. to 115° C.

The water content of the carbamate solution obtained from the first condensation compartment is typically 18-24 wt. %, preferably 18-21 wt. %, more preferably 19.0 wt. % or less, e.g. at 110-120° C. shell side outlet temperature.

Preferably, the plant comprises no dedicated $NH_3$ condenser. Very elegantly, sufficient condensation of the MP gas stream can be obtained in the first condensation compartment, thereby avoiding the need to use an additional MP carbamate condenser. By utilizing water evaporation from urea solution in the first evaporation stage for withdrawing heat from the first condensation compartment, a cooling water consumption can advantageously be relatively low.

A non-condensed gas from the first condensation compartment is for instance supplied, after gas/liquid separation from the MP carbamate solution, to a medium pressure (MP) scrubber, where it is e.g. scrubbed with the carbamate solution from the LP recovery section. The resulting liquid can be returned to the first condensation compartment.

The gas stream from the MP scrubber is advantageously small and is e.g. supplied to an absorber, in particular to a low pressure (LP) absorber.

The MP carbamate solution from the first condensation compartment is typically recycled to the HP synthesis section using a pump, e.g. to the pool condenser.

The condensation of the MP gas stream is carried out in indirect heat exchanging contact, i.e. through a heat exchanging wall, with a urea solution to be heated to give a heated urea solution. The urea solution to be heated is present in the first evaporation stage. The initial water content of the urea solution is e.g. 10-35 wt. %. The tube side pressure is typically 0.2-0.50 bara, preferably 0.25-0.35 bara. The urea solution is typically concentrated, by said heating by indirect heating exchange with condensing MP gas stream, and resulting water evaporation from the urea solution, to a concentration of at least 90 wt. % (urea+biuret), or at least 92 wt. % (urea+biuret), and for instance less than 96 wt. % urea (including biuret). Hence, typically such urea concentrations are achieved at the downstream end of the first evaporation stage. The urea solution from the first evaporation stage can also be referred to as urea melt.

Typically, the first condensation compartment and the first evaporation stage are configured for opposite flow at both sides of the heat exchanging wall, for instance with a falling film in the evaporation stage and upward flow in the condensation compartment.

The urea solution is typically concentrated in the first evaporation stage to the maximum urea content achievable by indirect heat exchange with the first condensation compartment which is at the condensation temperature while maintaining sufficient temperature difference over the heat exchanging wall.

The urea solution to be heated for example has at least 60 wt. % (urea+biuret) at the inlet of the first evaporation stage, for instance in the range 65-75 wt. % (urea+biuret).

The urea solution is e.g. subjected to a sub-atmospheric flash upstream of the first evaporation stage to remove $NH_3$.

A urea solution tank may be present between the LP decomposer and the first evaporation stage, typically downstream of a sub-atmospheric flash.

The second tube bundle of the horizontal pool condenser is used for raising steam, typically LP steam with a pressure in the range of 3.5-8.5 bar, typically e.g. 4-5 bar.

This LP steam is preferably used, at least in part, for further heating of the heated urea solution in a second evaporation stage; preferably by supplying the steam to a second condensation compartment in indirect heat exchanging contact with the second evaporation stage, i.e. through a heat exchanging wall, such as the walls of the tubes.

Preferably, a part, not all, of the LP steam that is raised in the second tube bundle is supplied to, and/or condensed in, the second condensation compartment, e.g. 1-20 wt. % of the LP steam, for instance 1-10 wt. % of the LP steam, or for instance 5-15 wt. % of the LP steam; more preferably in combination with a third evaporation stage using MP steam. MP steam is for example extracted from a HP $CO_2$ compressor.

The remaining part of the LP steam from the second tube bundle, e.g. at least 80 wt. % of that steam can be used, for instance, for LP steam consuming units such as, for example, ejectors, the LP decomposer, a wastewater treatment section, and steam tracing.

Preferably, the tubes of that heat exchanger have an inlet at the top for urea solution, and preferably the first condensation compartment is arranged above the second condensation compartment.

Preferably, the indirect heat exchange with the steam, in particular condensing steam, provides for an increase of the urea (including biuret) content of the heated urea solution by at least 1.0 wt. % (percent point), e.g. from 94 wt. % to at least 96 wt. % urea (including biuret), by water evaporation. The urea content increase is achieved in the second evaporation stage. Preferably, the urea content (including biuret) increases by max 5.0 wt. % (percent point) in the second evaporation stage, or max 2.0 wt. %, e.g. from 95 wt. % to 96 wt. %. Preferably only a relatively small part of the LP steam from the second tube bundle, e.g. 1.0-20 wt. %, is condensed in the second condensation compartment, or 1.0-10 wt. %, or even 1.0-5 wt. % of that LP steam, to better control the urea content of the urea melt from the second evaporation stage. Thereby the second evaporation stage is used for process control to accommodate fluctuations gas condensation in the first condensation compartment. It was surprisingly found that the combination of the first and second evaporation stage together with the preferred relatively low stripping efficiency of the HP stripper, e.g. less than 70%, or e.g. 55%-65%, or e.g. 60%-65%, provides that sufficient LP steam available for LP steam consuming equipment such as ejectors, the LP decomposer, a wastewater treatment section, and steam tracing, and while obtaining an advantageously high and controlled urea content of the urea melt (e.g. above 95 wt. % urea including biuret), even if only 1.0-20 wt. % of the LP steam from the second tube bundle is condensed in the second condensation compartment.

Especially in combination with a preferred downstream third evaporation stage using e.g. MP steam, preferably only a relatively small part of the LP steam from the second tube bundle, e.g. 1.0-20 wt. %, is condensed in the second condensation compartment, or 1.0-10 wt. %, or even 1.0-5 wt. %, especially in combination with a preferred downstream third evaporation stage using MP steam. It was surprisingly found that the combination of the first, second, and third evaporation stages and a relatively low stripping efficiency of the HP stripper, e.g. less than 70 wt. %, or 55%-65%, or e.g. 60%-65%, permits having sufficient LP steam available for equipment such as ejectors, the LP decomposer, a wastewater treatment section, and steam tracing and while obtaining an advantageously very high urea content of the urea melt (above 99 wt. % urea including biuret) from the third evaporation stage.

The urea solution (melt) at the outlet of the second evaporation stage for example has a concentration of less than 98 wt. % urea (including biuret).

The temperature in the second condensation compartment is e.g. at least 135° C., e.g. 135-160° C., and the temperature in the second evaporation stage is e.g. at least 130° C., for instance 130-140° C., or 130-135° C.

The maximum temperature in the second condensation compartment is for instance at least 5° C. higher or at least 10° C. higher than the maximum temperature in the first condensation temperature.

The urea solution preferably has the same pressure in the first and in the second evaporation stage. The first and the second evaporation stage may be provided in a single shell-and-tube heat exchanger having a tube bundle and a divided shell with the first condensation compartment of the shell space at the inlet of the tubes and the second condensation compartment of the shell space at the outlet of the tubes. Accordingly, in some embodiments, the first and the second evaporation stage are provided by two zones of tubes of a tube bundles, wherein these zones are not separated on the tube side but are defined by different heating fluids on the shell side. The first and the second evaporation stage may also be provided by two separate heat exchangers.

In some embodiments, the urea solution (e.g. urea melt) from the second evaporation stage has a urea content (including biuret) of at least 96.0 wt. % and hence can be used in a granulation unit without a need for a further urea content increase, for instance in a granulation unit with film spray nozzles, e.g. as described in U.S. Pat. No. 4,701,353.

In some embodiments, the urea solution (e.g. urea melt) from the second evaporation stage is further concentrated by heating at a lower pressure, e.g. a pressure of less than 0.30 bara or less than 0.10 bara, for instance to a urea concentration of at least 97.0 wt. % or at least 99.0 wt. % urea (including biuret), e.g. to 99.7 wt. % urea (including biuret) and the resulting urea melt is e.g. supplied to a prilling tower, a pastillation unit, or to a granulator. The heating at a preferred pressure of less than 0.10 bara is carried out e.g. in a third evaporation stage, which is e.g. a shell-and-tube heat exchanger.

Preferably, the urea melt at the inlet of the third evaporation stage has a urea concentration of less than 98 wt. % or less than 97 wt. % (including biuret). Preferably the third evaporation stage provides for an increase of the urea content by at least 1.0 wt. % (percent point), and/or to at least 98.5% or above 99.0 wt. % urea (including biuret). The third evaporation stage preferably is a shell-and-tube heat exchanger using steam as heating fluid, more preferably MP steam having a pressure of 5-10 bar, e.g. 8-10 bar. Hence, the third evaporation stage uses typically a different heating fluid than the second evaporation stage. The third evaporation stage operates at a lower pressure, for urea melt, than the second evaporation stage.

In an embodiment, the third evaporation stage uses MP steam of e.g. 8-9 bara, providing a urea melt with at least 98.5 wt. % urea including biuret, e.g. less than 1.5 wt. % water. The third stage evaporator operates e.g. at above 135° C., e.g. at about 140° C., and/or at a pressure of less than 15 kPa, e.g. 1-5 kPa or 5-15 kPa of the urea melt. A pressure of 1 to 5 kPa is for example used to prepare a urea melt, with e.g. at least 99.5 wt. % urea including biuret and/or e.g. less than 0.5 wt. % moisture which is suitable for e.g. prilling and pastillation. A pressure of 10 to 15 kPa is for example used to prepare a urea melt, with a moisture content of e.g. 1.0 to 3 wt. %, which is suitable e.g. for fluidized bed granulation.

By virtue the low water content of the resulting urea solution (from the second evaporation stage or the optional third evaporation stage), the urea solution is e.g. supplied to a granulation unit, preferably to a fluidized bed granulation unit. The urea solution as obtained from the tubes, in particular from the second evaporation stage, can be referred to as urea melt.

The vapour that is released in the tubes (of the first and second evaporation stage) comprises mainly $H_2O$ and $NH_3$ and is separated from the urea solution and is typically condensed as ammoniacal water, typically in a vacuum condenser. The resulting ammoniacal water is for instance used in part as an absorbent in an absorber, in particular in an LP absorber. The ammoniacal water can be added in part to the urea solution to be heated upstream of or inside the first evaporation stage.

The ammoniacal water comprises e.g. 2 to 10 wt. % $NH_3$, for instance 4 to 7 wt. % $NH_3$, and comprises at least 90 wt. % $H_2O$.

The HP carbamate condenser comprises a first and a second horizontal tube bundle, preferably both the first and the second tube bundle are U-shaped tube bundles. Each tube bundles comprises horizontal legs. In some embodiments, the first tube bundle is vertically stacked above the second tube bundle. In some embodiments, the second tube bundle (for raising steam) is vertically stacked above the first tube bundle (for heating MP urea solution).

In an example embodiment, the HP carbamate condenser comprises two U-shaped tube bundles arranged with, from bottom to top, the configuration ABBA, BAAB, AABB, or BBAA, wherein A are the straight legs of the first tube bundle (in operation having urea solution in the tubes) and B are the straight legs of the second tube bundle. In case of ABBA, the first tube bundle is looped around the second tube bundle, which is preferred. In case of BBAA, the first tube bundle is arranged above the second tube bundle. Configuration ABBA is preferred because the larger bend of the first tube bundle, in operation receiving urea solution, allows for easier cleaning inside the tubes in case of fouling inside the tubes.

The HP stripper is preferably operated with a stripping efficiency (alpha; a) of 70% or less, e.g. 58-70%; preferably max. 65%, e.g. 55%-65%, or e.g. 60%-65%, for example about 61%. A stripping efficiency higher than 70% is also possible, but is less advantageous.

The skilled person understands that "stripping efficiency" refers to the urea purity at the stripper liquid outlet and not to the energy efficiency of the stripper.

The stripping efficiency indicates the amount of ammonia converted to urea (and biuret) divided by the total amount of ammonia, typically measured at the liquid outlet of the stripper. This definition is equivalent to that of the $NH_3$ conversion based on the outlet of the stripper.

High pressure stripping with a relatively low stripping efficiency (e.g. a of less than 75%) requires significantly less heat, i.e. advantageously provides for a much lower steam consumption in the HP stripper. The HP stripper typically has an inlet for steam at the shell side, e.g. for MP steam, e.g. of at least 20 bar. The steam may be extracted from a high pressure (HP) $CO_2$ compressor of the urea plant, but may also be provided by a utility plant.

In addition, the high pressure stripping involves lower temperatures of the urea solution with preferred lower striping efficiency and this reduces hydrolysis of urea in the stripper compared to stripping at higher stripping efficiency. The reduced hydrolysis provides effectively for a conversion increase or at least a urea yield increase. Accordingly, the flow of feed ($CO_2$ and $NH_3$, in kg/h) can be reduced (for same urea production in kg/h), which provides for a longer residence time in the reaction zone (for a fixed equipment size for the reaction zone). This further increases the urea conversion (or urea yield). In an example embodiment, in total about 7% to about 10% extra urea production capacity can be achieved (based on constant reaction zone volume), or alternatively the reaction zone can be 7%-10% by volume smaller with the same urea production capacity. The reaction zone is often provided as a reactor of urea grade steel, which is an expensive construction material.

Furthermore, with lower stripping efficiency, the heat exchange duty (condensation duty) of a high pressure carbamate condenser (HPCC) is reduced. This may provide, for instance, for a smaller heat exchanging surface area (e.g. smaller tube bundle) or, in case of a fixed heat exchanging surface area, for an increase in the pressure of the steam raised in the HPCC. However, advantageously still sufficient medium pressure dissociation can be achieved in the first tube bundle and the carbamate level of the urea solution at the outlet of the first tube bundle is low enough to permit feeding to the LP recovery section, possibly after adiabatic MP stripping.

Preferably, in the HP stripper, of the $CO_2$ stripping type, the shell side temperature is in the range 194-200° C., preferably at 195° C.; i.e. these temperatures refer in particular to the compartment of the HP stripper that receives steam as heating fluid.

Lower stripping efficiency advantageously also provides for reduced biuret formation over the stripper, in particular with 0.05-0.1 wt. % less biuret, as wt. % of the final urea product; e.g. with 0.65-0.85 wt. % biuret in the final urea product.

Lower stripping efficiency causes more carbamate recycle downstream of the HP stripper, but this carbamate is advantageously decomposed in a great part at medium pressure in the first tube bundle and condensed in the MP section in heat exchanging contact with the urea solution to be heated such that the resulting MP carbamate solution can have relatively lower water fraction (wt. %); and this MP condensation also contributes to an advantageous high degree of water evaporation from the urea solution in the first evaporation stage.

Advantageously, the water content of the LP carbamate solution supplied to the first condensation compartment is sufficient to prevent carbamate crystallization in the first condensation compartment.

Advantageously, the reaction zone outlet H/C ratio is e.g. max. 0.60, or max. 0.55, or max. 0.50, and for instance in the range 0.40-0.50.

Preferably, an aqueous stream is added to the urea solution to be heated, wherein said aqueous stream is added upstream of or inside the first evaporation stage; more preferably upstream of the first evaporation stage. The aqueous stream comprises e.g. at least 90 wt. % $H_2O$ and e.g. 3-10 wt. % $NH_3$ and is e.g. ammoniacal water. Preferably, the aqueous stream is added in an amount providing a decrease of the urea content (including biuret) of at least 2.0 percent point by weight, e.g. from 72 wt. % (urea+biuret) to 70 wt. % (urea+biuret), referring to the urea content (including biuret) at the inlet of the first evaporation stage. Typically, the decrease is less than 10 percent point by weight.

For example, the amount of water added is at least 5 wt. % of the amount of water already present in the urea solution. Preferably, the amount of water added is at least 1.0 wt. % of the urea solution to be heated, and/or preferably max 10 wt. % of the urea solution to be heated.

Counterintuitively, adding water to a urea solution that is supplied to an evaporation stage, which stage is used for evaporating water, was found to provide advantageous results, in particular in combination with the preferred lower stripping efficiency of the HP stripper. Lower stripping efficiency provides for more carbamate in the stripped urea solution and hence more carbamate to be condensed in the first condensation compartment. The first condensation compartment operates at the condensation point, i.e. fixed temperature for given pressure and composition; with medium pressure contributing to sufficient carbamate decomposition in the first tube bundle. On the other hand, the urea solution to be heated typically originates from the LP recovery section thereby having a given amount and composition. Moreover, sufficient temperature difference must be maintained between both sides of a heat-exchanging wall between the first condensation compartment and the first evaporation stage to allow for the heat exchange. The added water very elegantly enables sufficient carbamate condensation in the first condensation compartment even with lower stripping efficiency.

The aqueous stream originates e.g. from a condenser of the evaporation section or e.g. from an absorber.

The aqueous stream is for instance the ammoniacal water from said vacuum condenser. The added aqueous stream originates for instance from the LP or atmospheric absorber. The atmospheric absorber may receive vapours e.g. from steam ejectors and vacuum condensers, or e.g. the non-condensed gas from the LP carbamate condenser. The LP absorber may receive vapour e.g. from the first condensation compartment. An absorber is for instance used for contacting a vapour with water (such as purified process condensate from a WWT section).

The water content of the urea solution is increased upstream of the evaporation section in this preferred embodiment to ensure, very elegantly, that sufficient MP gas can be condensed by heat exchange with the urea solution, especially with the relatively low stripping efficiency of the HP stripper and the relatively high condensation temperature of the MP gas. This provides for increased flexibility, in particular to adapt to changes in the stripping efficiency of the HP stripper, without any structural modifications of the HP carbamate condenser being necessary and without any risk of upsetting the LP steam formation in the second tube bundle.

In preferred embodiments wherein ammoniacal water is added to the urea solution, the inclusion of $NH_3$ in the added water may advantageously contribute to suppressing biuret formation in the first evaporation section and possibly also in the second evaporation stage. For instance, the biuret formation over the first evaporation stage may be decreased by at least 5%, e.g. 5-15%, relative to the amount of biuret formed in the first evaporation stage without the addition of ammoniacal water.

Furthermore, advantageously the liquid residence time of the urea solution in the tubes can be relatively short, thereby reducing biuret formation.

The urea solution from the second evaporation stage, in particular the urea melt from the second evaporation stage, is preferably supplied, directly or indirectly, to a finishing section. The finishing section is adapted for solidifying urea melt into solid urea product. The finishing section is for instance a granulation unit or a prilling tower. The granulation unit is for instance a fluidized bed granulation unit and has for instance film spray nozzles. Suitably, a third evaporation stage is provided between the second evaporation stage and the finishing section.

Vapour obtained from the first and the second evaporation stage, in particular water vapour, is typically condensed in a vacuum condenser to form an aqueous condensate. The aqueous condensate, which contains some $NH_3$ and urea, is for instance in part or entirely supplied to a waste water treatment (WWT) section. The WWT section preferably comprises a hydrolysis unit and a desorber, to give a purified process condensate. The purified process condensate is supplied, e.g., at least in part, to the LP or atmospheric absorber. The processing of water in the WWT is energy intensive.

In the present invention, preferably at least a part of the aqueous condensate is used as ammoniacal water that is added to the urea solution that is supplied to the first evaporation section. Thereby advantageously the load on the WWT is lower compared to other sources of the water such as the purified process condensate or the steam condensate. Very elegantly, the presence of $NH_3$ and possibly urea in the aqueous condensate is no problem when the condensate added to the urea solution.

The invention also pertains to a urea production plant (urea plant). The plant is preferably suitable for carrying out the inventive urea production process. The plant comprises a high pressure (HP) synthesis section. The HP section comprises a reaction zone, a carbamate condenser and a stripper. The reaction zone is e.g. a vertical urea reactor or a part of a combined vessel. The reaction zone may be provided by one or more units in series and/or in parallel. The carbamate condenser comprises a shell-and-tube heat exchanger, which comprises a shell space and a first and a second horizontal tube bundle. The stripper has a gas outlet for gas connected to an inlet of said shell space of the HP carbamate condenser. The plant also comprises an expansion device for expanding urea solution from said synthesis section to medium pressure (MP) to give a first MP urea solution. The plant preferably comprises a flash vessel for adiabatic flashing of the first MP urea solution.

The first tube bundle is configured for heating said first MP urea solution thereby decomposing carbamate comprised in said first MP urea solution. The plant comprises a fluid connection from the expansion device to an inlet of the first tube bundle. The plant comprises a gas/liquid separation unit connected to the outlet of said first tube bundle. The unit has an outlet for a second MP urea solution and an outlet for an MP gas stream. The plant preferably comprises an LP recovery section receiving the second MP urea solution, and preferably comprises an adiabatic MP stripping unit for stripping the second MP urea solution using vapour from the preferred adiabatic flashing.

The plant comprises a first condensation compartment for condensing said MP gas stream; a first evaporation stage for heating a urea solution to be heated in indirect heat exchanging contact with said first condensation compartment to give a heated urea solution. The plant preferably comprises a second evaporation stage for further heating the heated urea solution, more preferably in indirect heat exchanging contact with steam from the second tube bundle. The plant preferably comprises a flow line for urea solution from the LP recovery section to the first evaporation stage.

The inventive urea plant (urea production plant) comprises a supply line for adding an aqueous stream to the urea solution to be heated, to add said aqueous stream upstream of or in the first evaporation stage. Hence, the aqueous stream is added to the urea solution that is to be heated, in particular to urea solution that is to be heated in the first evaporation stage. Hence, the supply line allows for combining the urea solution with the aqueous stream at a position upstream of the first evaporation stage, or in the first evaporation stage. The urea solution to be heated is typically the urea solution from the LP recovery section.

The supply line is preferably arranged upstream of the first evaporation stage, e.g. connected to the flow line for urea solution from the LP recovery section to the inlet of the first evaporation stage, and more preferably downstream of the atmospheric flash, if any, between the LP recovery section and the first evaporation stage. The supply line is a liquid flow line. The supply line is preferably connected to the tubes (tube side) of the preferably used shell-and-tube MP carbamate condenser; said tubes providing the first evaporation stage.

The supply line is connected to a unit providing the aqueous stream, more preferably said aqueous stream is provided at least in part by said ammoniacal water. In an embodiment, the plant comprises an absorber having a liquid outlet connected to said supply line. The absorber is e.g. an LP or atmospheric absorber, as described further herein. In a preferred embodiment, the plant comprises a vacuum condenser having a liquid outlet connected to said supply line. Advantageously, thereby the aqueous condensate from the vacuum condenser does not need to be supplied to a waste water treatment (WWT) section, at least for the part of water that is sent to the supply line.

The invention also pertains to a method of modifying an existing urea plant. The existing urea plant preferably comprises or is modified to comprise:
- a high pressure (HP) synthesis section comprising a reaction zone, a carbamate condenser and a stripper, wherein the carbamate condenser comprises a shell-and-tube heat exchanger comprising a shell space and a first and a second horizontal tube bundle, wherein the stripper has a gas outlet for gas connected to an inlet of said shell space,
- an expansion device for expanding urea solution from said synthesis section to medium pressure (MP) to give a first MP urea solution,
- wherein the first tube bundle is configured for heating said first MP urea solution thereby decomposing carbamate comprised in said first MP urea solution,
- a gas/liquid separation unit connected to the outlet of said first tube bundle and having an outlet for an MP liquid stream and an outlet for an MP gas stream,
- a first condensation compartment for condensing said MP gas stream,
- a first evaporation stage for heating a urea solution to be heated in indirect heat exchanging contact with said first condensation compartment to give heated urea solution,
- preferably a second evaporation stage for further heating the heated urea solution, more preferably in indirect heat exchanging contact with steam from the second tube bundle.

The method involves adding to the plant a supply line for adding an aqueous stream to the urea solution to be heated, configured for adding said aqueous stream upstream of or in the first evaporation stage, preferably upstream of the first evaporation stage. In some embodiments, the added supply line is connected to a liquid outlet of an absorber. In the existing urea plant, the absorber has for instance a liquid outlet connected with a waste water treatment (WWT) section. In a preferred embodiment, the added supply line is connected to a liquid outlet of a vacuum condenser.

Preferably, the method gives the urea plant according to the invention. All preferences for the inventive urea plant, apply also for the modified plant.

The term "existing urea plant" is used without implying that the specified features of the existing plant are part of the state of the art and without admitting any prior art.

FIG. 1 illustrates and example plant and process according to the invention. An HP synthesis section comprises a reaction zone (1), an HP carbamate condenser (2), and an HP stripper (3). The HP stripper is preferably a $CO_2$ HP stripper. Generally, feed $CO_2$ is supplied to the $CO_2$ HP stripper. The reaction zone (1) is, as an example, comprised in the vessel (23) which also provides the HP carbamate condenser (2). Optionally, the reaction zone (1) is provided in part or entirely by an optional vertical reactor (25).

Urea synthesis solution (26) from the reaction zone (1) comprises urea, water and ammonium carbamate and is supplied to the stripper (3). Gas (7) from the stripper is supplied to the shell space (4) of the HP carbamate condenser (2) and is condensed therein in an exothermic reaction to form a HP carbamate solution (8) which is supplied as liquid stream to the reaction zone (1), for example internally in the vessel (23). The HP carbamate condenser (2) is a shell-and-tube heat exchanger comprising a first tube bundle (5) and a second tube bundle (6). The second tube bundle (6) is illustrated arranged above the first tube bundle (5) but other configurations are also possible. The first tube bundle (5) receives in the tubes a first MP urea solution (10) which solution also comprises carbamate. By the indirect heat exchange with the condensing process medium in the shell space (4), the carbamate in the urea solution is at least in part decomposed to form $CO_2$ and $NH_3$. The fluid (11) from the outlet of the first tube bundle is subjected to gas/liquid separation (12) to give an MP gas stream (14) and a second MP urea solution (13).

The MP gas stream (14) comprises $CO_2$ and $NH_3$ and is condensed in a first condensation compartment (15). The first condensation compartment (15) is in indirect heat exchanging contact, through a heat-exchanging wall, with urea solution (16) to be heated in the first evaporation stage (18). The first condensation compartment (15) is for instance a compartment in a shell side of a shell-and-tube heat exchanger with the urea solution to be heated (16) in the tubes. Preferably, also off-gas (27) from the HP carbamate condenser (2) is supplied to the first condensation compartment (15). MP carbamate solution (36) is supplied from the first condensation compartment (15) directly or indirectly to the HP synthesis section, in particular to the shell space (4).

Urea solution (9) from the synthesis section is expanded using an expansion device such as expansion valve (24), subjected to gas/liquid separation, e.g. in adiabatic flash unit (28) and supplied as the first MP urea solution (10) to the first tube bundle (5) of the carbamate condenser (2). In particular, typically the stripped urea solution (22) from the HP stripper (3) is expanded using the expansion device such as the expansion valve (24) to medium pressure and is subjected to gas/liquid separation, e.g. in the adiabatic flash unit (28). The flash vapour (29) is rich in $CO_2$, in particular with the adiabatic flashing of the urea solution stripped in a HP $CO_2$ stripper, and is supplied preferably to the first condensation compartment (15), typically after contacting with the liquid stream (13) (not shown).

The second MP urea solution (13) is typically supplied to the LP decomposer of a LP recovery section (30). Gas from the LP decomposer is condensed in an LP carbamate condenser (not shown) to form LP carbamate solution (31), also comprising water, which is preferably also supplied to the first condensation compartment (15). Typically, some water is added to the LP carbamate condenser to prevent crystallization (not shown). The LP urea solution (16) from the LP decomposer is preferably used as the urea solution (10) that is heated in the first evaporation stage (18). The LP urea solution (16) is typically transformed into urea melt (32) by heating and water evaporation. The heating is carried out in a first evaporation stage (18) which is in heat exchanging contact with the first condensation compartment (15). Heated urea solution (17) resulting from the first evaporation stage (18) is further heated in a second evaporation stage (20) preferably by heat exchanging with low pressure steam (19) that is raised in the second tube bundle (6) and that is supplied to the second condensation compartment (35) where the steam (19) at least in part condenses in indirect heat exchanging contact with the second evaporation stage (20).

Generally, the first (15) and the second (35) condensation comportment are separated from each other and hold different fluids in operation. Generally, the first (18) and the second (20) evaporation stage may be provided by one tube bundle. For instance, the first (15) and the second (35) condensation compartment and the first (18) and the second (20) evaporation stage are provided by a shell-and-tube condenser having a shell side divided in two compartments being the first (15) and the second (35) condensation compartment.

Generally, feed $NH_3$ is also supplied to the HP synthesis section, in particular to the HP carbamate condenser (2).

Urea melt (32) from the second evaporation stage (20) is optionally supplied to a finishing section (33) where it is solidified into solid urea product (34).

In a preferred embodiment, an aqueous stream is added, through a supply line (21), to the urea solution (16) that is supplied to the first evaporation stage (18).

The urea solution (16) is heated in the first evaporation stage (18) through indirect heat exchanging contact with fluid in the condensation compartment (15); hence the first evaporation stage (18) and the condensation compartment (15) are distinct and separated compartments.

In embodiments with a shell-and-tube heat exchanger that is operated with the urea solution to be heated (16) in the tubes and wherein the first condensation compartment (15) is a shell side compartment of said heat exchanger, the supply line (21) is connected to the tubes of said heat exchanger.

Preferably, a non-condensed gas (37) from the first condensation compartment (15) is supplied, optionally through an MP scrubber using the carbamate solution (31) from the LP recovery section as a scrub liquid, to an absorber (not shown) for removal of $NH_3$. The absorber also receives a water stream (such as cleaned process condensate).

Water vapour (39) from the evaporation stages is supplied to a vacuum condenser (38). In the example embodiment, process condensate from the vacuum condenser (38) is supplied at least in part to the aqueous stream via the supply line (21).

FIG. 1 also illustrates an embodiment with the optional vertical reactor (25) which in this embodiment provides a second part (la) of the reaction zone, and with a flow line (8) from the first part of the reaction zone provided in the vessel (23) to said second part (la). In embodiments without such a vertical reactor, e.g. with a pool reactor as the vessel (23), the urea synthesis solution (26) can be obtained directly from the vessel (23). In further embodiments wherein the optional vertical reactor (25) is used as the reaction zone (1), the HP carbamate solution (8) is supplied to the vertical reactor (25) and the urea synthesis solution (26) can be obtained from the vertical reactor (25).

Figure 2:
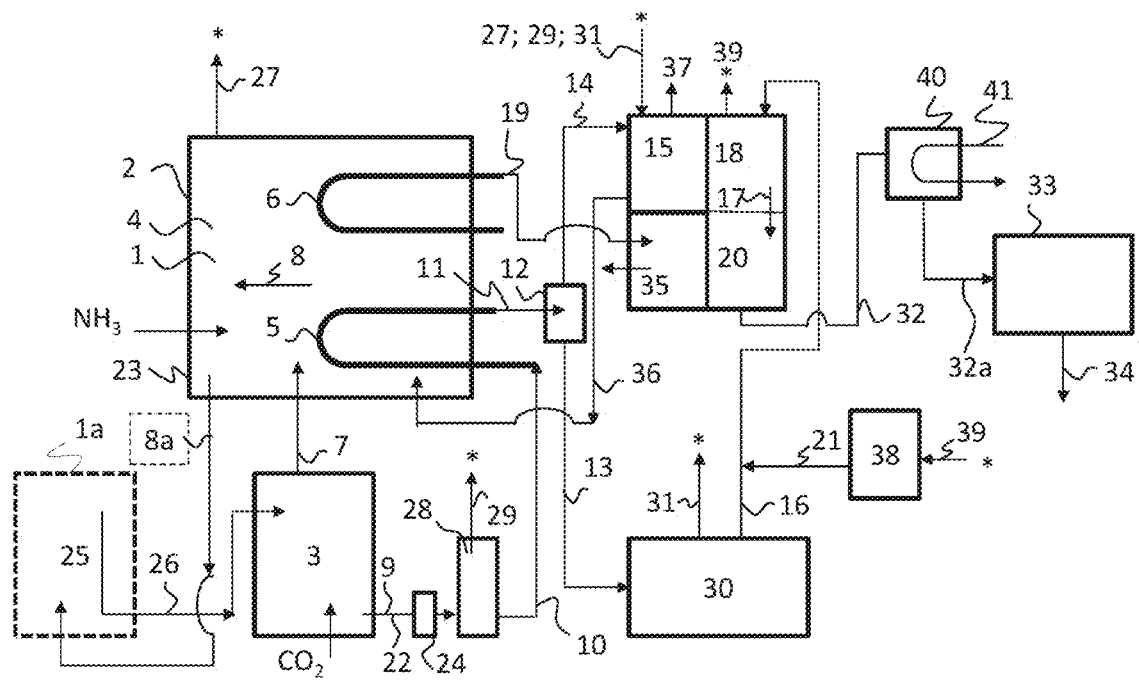
FIG. 2 schematically illustrates an example of a urea production process and a plant according to the invention.

FIG. 2 illustrates an embodiment wherein the urea melt (32), e.g. with 4 wt. % water, is further concentrated to a concentrated urea melt (32a) by water evaporation to a level of e.g. 0.3 wt. % water in a third evaporation stage (40). The third evaporation stage (40) is operated at a lower pressure, for urea solution, than the second evaporation stage (20) and uses indirect heat exchange with MP steam (41) of 8-9 bar as heating fluid. All other references are the same as in FIG. 1.

As used herein, the stripping efficiency alpha $(\alpha) = (2*wt. \% \text{ urea}/60)/((2*wt. \% \text{ urea}/60) + (wt. \% NH_3/17))$, measured at the liquid outlet of the stripper, wherein wt. % $NH_3$ includes all ammonia species including ammonium carbamate. Biuret is lumped with urea because the amounts of biuret are very low.

The N/C ratio ($NH_3:CO_2$ ratio) of the reaction zone reflects the composition of the so-called initial mixture before urea production, consisting only of $NH_3$, $CO_2$ and $H_2O$, as used in the art of urea plants, and is the molar ratio, and is measured at the outlet of the reaction zone for urea synthesis solution.

The N/C ratio for gas streams is the molar ratio of $NH_3$ to $CO_2$.

The N/C ratio for carbamate condensers, such as the first condensation compartment, is the molar ratio $NH_3$ to $CO_2$ including these components present as carbamate, determined at the outlet for carbamate liquid.

The H/C ratio of the reaction zone, as used herein, refers to the molar ratio $H_2O:CO_2$, in particular reflecting the composition of the so-called initial mixture. The H/C ratio is for instance as measured at the reactor outlet.

Carbamate, as used herein, refers to ammonium carbamate, as that term is used in the art.

As used herein, for process streams (i.e. not for steam lines), high pressure (HP) is above 100 bar, for instance 120 to 300 bar, typically 150 to 200 bar. Medium pressure (MP) is for example 10 to 70 bar (including intermediate pressure of 30 to 70 bar), in particular 15 to 30 bar, and low pressure (LP) is for example 0 to 10 bar, in particular 1 to 8 bar or 2 to 5 bar. All pressures are bar absolute (bara).

Condensation in a carbamate condenser refers to so-called carbamate condensation, which involves the reaction of $NH_3$ and $CO_2$ into carbamate forming carbamate solution. Carbamate decomposition refers to the dissociation reaction of carbamate into $NH_3$ and $CO_2$.

The terms 'typically' and 'preferably' and derived forms indicate non-mandatory features.

Preferably the urea production process is carried out in the inventive urea plant. All preferences for the urea production process apply equally for the urea plant. All preferences and details indicted for equipment parts in connection with the urea production process, apply equally for the urea plant.

In summary the invention pertains to a urea production process wherein carbamate in an MP urea solution is decomposed in a tube bundle of a high pressure carbamate condenser (HPPC) and a resulting gas is condensed in indirect heat exchange with a urea solution to be heated and wherein a HP stripper is preferably operated with relatively low stripping efficiency.

A preferred embodiment will now be illustrated by the following example, which does not limit the invention or the claims.

Example 1

A urea plant as generally illustrated in FIG. 2 with a prilling tower as finishing section was operated with 83.3 ton/hr urea production (equivalent to 2000 metric ton per day urea prills), with a HP $CO_2$ stripper operated with ~64% stripping efficiency. LP steam (19) was raised at 37 ton/hr in the second tube bundle (6), and used as follows: 11 ton/hr to ejectors, 8.5 ton/hr to the LP decomposer, 10 ton/hr to the waste water treatment section, 6.5 ton/hr to steam tracing/jacketing, and 1.0 ton/hr to the second condensation compartment (35) in heat exchange with the second evaporation stage (20). The first evaporation stage (18) provided for concentration of ~72 wt. % urea solution (~85° C.) to a melt with 94-95 wt. % urea (including biuret) at 130-135° C. (temperature given by process-process heat exchange) at 0.3 bara; the second stage evaporation provided for further concentration to 96 wt. % urea at a controlled temperature of 135° C. to fine-tune the urea concentration at the same pressure. The third evaporation stage is provided by a separate evaporator using MP steam to concentrate the melt to 99.7 wt. % at ~140° C.

The invention claimed is:

1. A process for the production of urea from ammonia and carbon dioxide in a urea plant,
    wherein the urea plant comprises a high pressure (HP) synthesis section comprising a reaction zone, a carbamate condenser and a stripper,
    wherein the carbamate condenser comprises a shell-and-tube heat exchanger with a shell space and a first and a second horizontal tube bundle,
    wherein the process comprises:
    forming a urea synthesis solution comprising urea, water and ammonium carbamate in said reaction zone,
    condensing gas from the stripper in the shell space thereby providing a carbamate-containing high pressure liquid stream;
    expanding said urea synthesis solution from said synthesis section to medium pressure (MP) to give a first MP urea solution comprising carbamate;
    heating said first MP urea solution in said first tube bundle, thereby decomposing said carbamate comprised in said first MP urea solution;
    subjecting a fluid stream from the outlet of said first tube bundle to gas/liquid separation to give a second MP urea solution and an MP gas stream;
    condensing said MP gas stream at medium pressure in a first condensation compartment thereby forming carbamate and heating through indirect heat exchanging contact a urea solution to be heated giving heated urea solution in a first evaporation stage; and
    raising steam in said second tube bundle and using said steam to further heat through indirect heat exchanging contact said heated urea solution in a second evaporation stage.

2. The process according to claim 1, wherein said stripper is operated with a stripping efficiency alpha (a) of 70% or less.

3. The process according to claim 2, further comprising adding an aqueous stream to the urea solution to be heated upstream of, or inside, said first evaporation stage.

4. The process according to claim 3, wherein said aqueous stream is ammoniacal water comprising 1.0-10.0 wt. % $NH_3$.

5. The process according to claim 3, wherein the aqueous stream is added in an amount providing for a decrease of 2-10 percent by weight of the urea content of the urea solution at the inlet of the first evaporation stage.

6. The process according to claim 1, wherein the stripper is a $CO_2$ stripper.

7. The process according to claim 1, wherein the urea solution that is expanded from said synthesis section to medium pressure, is stripped urea solution from the stripper.

8. The process according to claim 1, wherein said carbamate condenser and said reaction zone are provided by a single vessel.

9. The process according to claim 1, further comprising the steps of concentrating the urea solution from the second evaporation stage by heating in a third evaporation stage at a pressure of less than 0.30 bar to a urea concentration of at least 97.0 wt. % urea including biuret and supplying the resulting urea melt to a prilling tower, a pastillation unit, or to a granulator.

10. The process according to claim 9, wherein the third evaporation stage comprises using medium pressure steam.

11. The process according to claim 10, wherein 1-20 wt. % of the steam raised in said second tube bundle is used to further heat through indirect heat exchanging contact said heated urea solution in the second evaporation stage.

12. A urea plant comprising:
    a high pressure (HP) synthesis section comprising a reaction zone, a carbamate condenser and a stripper, wherein the carbamate condenser comprises a shell-and-tube heat exchanger comprising a shell space and a first and a second horizontal tube bundle, wherein the stripper has a gas outlet for gas connected to an inlet of said shell space;
    an expansion device for expanding a urea solution from said synthesis section to medium pressure (MP) to give a first MP urea solution;
    wherein the first tube bundle is configured for heating said first MP urea solution thereby decomposing carbamate comprised in said first MP urea solution;
    a gas/liquid separation unit connected to the outlet of said first tube bundle and having an outlet for a second MP urea solution and an outlet for a MP gas stream;
    a first condensation compartment for condensing said MP gas stream;
    a first evaporation stage for heating a urea solution to be heated in indirect heat exchanging contact with said first condensation compartment to give a heated urea solution; and
    a second evaporation stage for further heating the heated urea solution in indirect heat exchanging contact with steam from the second tube bundle.

13. The urea plant according to claim 12, comprising a supply line for adding an aqueous stream to the urea solution to be heated upstream of or in the first evaporation stage.

14. The urea plant according to claim 13, comprising an absorber having a liquid outlet connected to said supply line.

15. The urea plant according to claim 13, comprising a vacuum condenser having a liquid outlet connected to said supply line.

16. The urea plant according to claim 12, wherein said stripper is a $CO_2$ stripper.

17. The process according to claim 1, wherein the steam is at least in part condensed in a second condensation compartment in indirect heat exchanging contact with said heated urea solution in said second evaporation stage.

18. The process according to claim 2, wherein said stripper is operated with a stripping efficiency alpha (a) of 65% or less.

19. The process according to claim 2, wherein said stripper is operated with a stripping efficiency alpha (a) of 55-65%.

20. The process according to claim 8, wherein said carbamate condenser and said reaction zone are provided by a pool reactor.

* * * * *